United States Patent [19]

Labeeuw et al.

[11] Patent Number: 4,464,367
[45] Date of Patent: Aug. 7, 1984

[54] CEPHALOSPORIN DERIVATIVES, PROCESS FOR PREPARATION THEREOF AND DRUGS CONTAINING SAID DERIVATIVES USABLE AS ANTIBIOTICS

[75] Inventors: Bernard Labeeuw, Montpellier; Ali Salhi, St. Gely Du Fesc, both of France

[73] Assignee: Sanofi, Paris, France

[21] Appl. No.: 245,328

[22] Filed: Mar. 19, 1981

[30] Foreign Application Priority Data

Mar. 26, 1980 [FR] France .................. 80 06757

[51] Int. Cl.³ .................. A61K 31/545; C07D 501/56
[52] U.S. Cl. ........................... 424/246; 544/27
[58] Field of Search ........................ 544/27; 424/246

[56] References Cited

U.S. PATENT DOCUMENTS

| 4,097,595 | 6/1978 | Heymes | 424/246 |
| 4,202,893 | 5/1980 | Heymes et al. | 544/27 |
| 4,278,793 | 7/1981 | Durckheimer et al. | 544/27 |

FOREIGN PATENT DOCUMENTS

| 866038 | 10/1978 | Belgium . |
| 2345153 | 10/1977 | France . |
| 78/2168 | 12/1978 | South Africa . |
| 1581184 | 12/1980 | United Kingdom . |

*Primary Examiner*—Paul M. Coughlan, Jr.
*Attorney, Agent, or Firm*—Schwartz, Jeffery, Schwaab, Mack, Blumenthal & Koch

[57] ABSTRACT

The invention relates to derivatives of the family of cephalosporins, to a process for preparation thereof and to the therapeutic application thereof. The compounds of the invention correspond to formula:

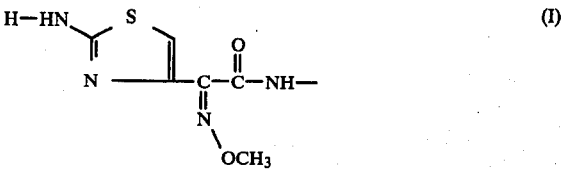

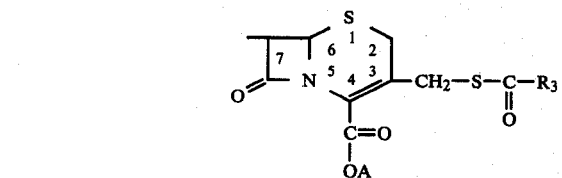

in which:

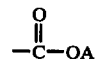

is an acid, an alkaline or alkaline-earth salt, an amine salt or an ester;

$R_3$ is furyl or thienyl.

12 Claims, No Drawings

CEPHALOSPORIN DERIVATIVES, PROCESS FOR PREPARATION THEREOF AND DRUGS CONTAINING SAID DERIVATIVES USABLE AS ANTIBIOTICS

The present invention relates to derivatives of the family of cephalosporins, to a process for preparation thereof and to their application in therapeutics.

The compounds according to the invention correspond to formula:

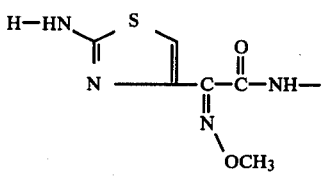

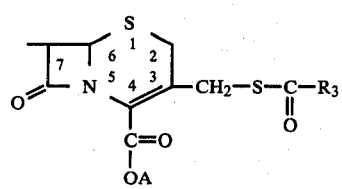

in which: the group

in 4 position is an acid radical, or an alkaline or alkaline-earth salt or an amine salt, for example triethylamine or the ethanolamines, or an ester radical easily hydrolysable or metabolically labile and pharmaceutically acceptable; and $R_3$ is a radical chosen from furyl

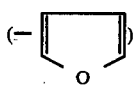

and thienyl

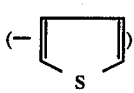

radicals.

Due to the presence in the formula of an oxime group, compounds (I) exist in two syn and anti isomer forms. The syn isomers, of which the therapeutic activity is superior, are the preferred compounds.

It is understood that compounds (I) indicated hereinabove may exist:
either in the form indicated in formula (I)
or in the tautomeric form (I'):

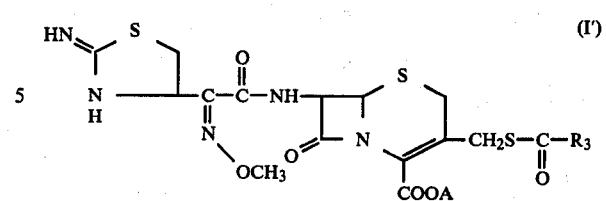

in which A and $R_3$ have the meanings indicated previously.

The invention also relates to a process for preparing the compounds of formula (I) which comprises the acylation of an amino-7 cephalosporin of formula:

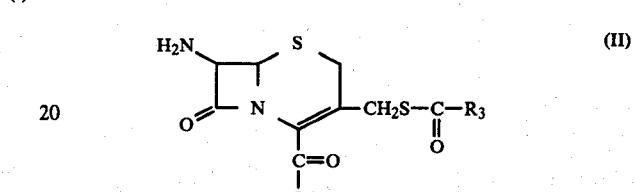

by the acid:

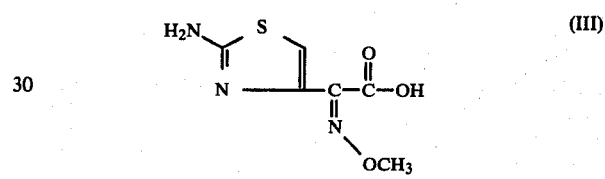

Before effecting the acylation reaction, it is desirable to substitute the amino group of the acid by a protector group easy to eliminate subsequently. The group usually used in organic synthesis for the protection of the amino groups and in particular the trityl group, may be used.

To effect the acylation reaction, it is necessary to activate the carboxyl group of compound (III), preferably by conversion into anhydride with the aid of a carbodiimide, generally dicyclohexylcarbodiimide.

The activation reaction is effected within a suitable organic solvent such as tetrahydrofuran at a temperature of between 0° and 50° C. and preferably at ambient temperature. The activation reaction is possibly facilitated by addition of a hydroxylated derivative such as hydroxy-1 benzotriazole.

The solution of the acylation reagent thus obtained, freed, by filtration, of the dicyclohexylurea formed, is added to a solution of compound (II) in a solvent such as aqueous tetrahydrofuran and in the presence of an alkaline agent such as triethylamine. The addition of the two reagents may also be made in the reverse order.

After the acylation reaction, the protector group is eliminated by a known process, particularly by hydrolysis in an acid medium, using an organic acid such as formic acid or trifluoroacetic acid.

Concerning the raw materials of the reaction, compound (III) and its derivatives in which the amino group is blocked by a protector group, are known.

The products of formula (II) are known or may be prepared according to a known process by action of a thioacid on the amino-7 cephalosporanic acid:

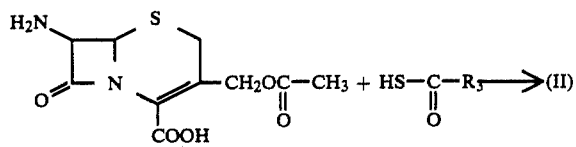

The thioacids of which certain are known may be obtained by action of an alkaline sulfhydrate on the chloride or a mixed anhydride of the corresponding acid according to the method described in the Journal of Antiobiotics 27, 573–8, (1974) or by action of hydrogen sulfide in pyridine or triethylamine on the chloride or a mixed anhydride of the corresponding acid.

According to a variant of the process, compounds (I) may be obtained from the amino-7 cephalosporanic acid and acid (III) which lead to compound (IV). By action on (IV) of thioacid

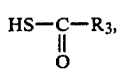

the compounds (I) of formula:

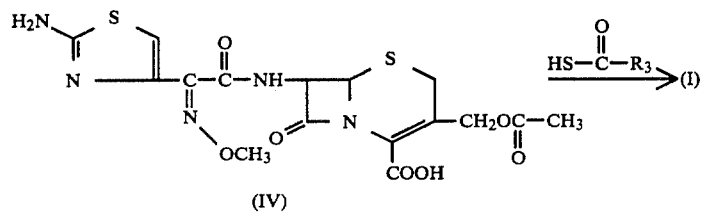

are obtained.

Compounds (I) of the invention in which A is other than H are obtained from the compounds (I) in which A is H by reactions known per se.

Thus, the mineral salts are obtained by action on compounds (I) in which A is H of a mineral base such as sodium hydroxide or potassium hydroxide or sodium bicarbonate in equimolecular quantity; the salification reaction is effected in a solvent such as water or ethanol and the salt obtained is isolated by evaporation of the solution.

The salts of organic bases are obtained by action, on a solution of the acid (I, A=H) in a solvent or a suitable mixture of solvents, of an equimolecular quantity of the organic base. The salt is isolated by precipitation with ether.

The esters are obtained by the known processes of esterification; for example, the action of a halogen derivative on a salt such as the sodium salt of the acid will advantageously be used; the reaction will preferably be effected in a solvent capable of dissolving the starting acid derivative for example in dimethylformamide.

The isomers of syn and anti form are obtained by a suitable choice of the reagents.

The following examples will enable the scope of the invention to be more readily understood.

As is usual in this family of compounds, the products according to the invention do not have a clear melting point, but only points of decomposition which do not enable them to be characterised.

The products will therefore be characterised by their nuclear magnetic resonance spectrum recorded at 60 MHz, the internal standard being hexamethyldisiloxane.

The following abbreviation will be used:
S : singlet
D : doublet
D of D : doublet of doublet
S el : broadened singlet
AB : system AB
J : represents the coupling constant.

Moreover, the elementary microanalyses were carried out in each case and are in accordance with the formulae indicated.

EXAMPLE 1

Syn isomer [(amino-2 thiazolyl-4)-2 methoxyimino-2 acetamido]-7 (furyl-2 carbonylthiomethyl)-3 cepheme-3 4-carboxylic acid (CM 31916)

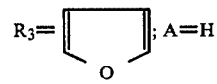

(a) Syn isomer [(tritylamino-2 thiazolyl-4)-2 methoxyimino-2 acetamido]-7 (furyl-2 carbonylthiomethyl)-3 cepheme-3 4-carboxylic acid To a suspension of 44.3 g of syn isomer (tritylamino-2 thiazolyl-4)-2-methoxyimino-2 acetic acid in 400 ml of anhydrous tetrahydrofuran are added 20.6 g of dicyclohexylcarbodiimide and 13.5 g of hydroxy-1 benzotriazole. Stirring is effected for 45 minutes at ambient temperature then the dicyclohexylurea formed is filtered off.

The solution thus prepared is added with stirring and under a nitrogen atmosphere for 45 minutes to a solution of 28 g of amino-7 (furyl-2 carbonylthiomethyl)-3 cepheme-3 4-carboxylic acid and 12 ml of triethylamine in 140 ml of icy water and 140 ml of tetrahydrofuran. For the whole duration of the addition and 30 minutes after the end thereof, the temperature is maintained about 5° C. by an ice bath and the pH is maintained at 8.9 by addition of a 30% (volume/volume) solution of triethylamine in the (50—50) mixture of tetrahydrofuran-water.

The mixture is then left with stirring at ambient temperature for 20 hours. The tetrahydrofuran is evaporated in vacuo and the residue is firstly extracted with 350 ml of methylene chloride, then a second time with 150 ml of the same solvent. The organic extracts are combined, 100 ml of water are added and the mixture is acidified to pH 2 by addition of a 6 N hydrochloric acid solution. The aqueous phase is decanted, the organic solution is washed with 200 ml of water then dried over magnesium sulfate. The solid is dried without heating and rinced with ether, the product obtained is purified by dissolution in 150 ml of methylene chloride and reprecipitation by 400 ml of ether.

Finally, 39.8 g of the expected product are obtained. By addition of more ether, a second jet (3.2 g) is isolated.

NMR spectrum (in solution in dimethylsulfoxide): 1 H at 9.55 ppm (N$\underline{\text{H}}$ CO, D, J=8 Hz)—1 H at 8.90 ppm (N$\underline{\text{H}}$ Trit.S.el)—1 $\overline{\text{H}}$ at 8.0 ppm (H$_5$ furan, S)—16 H at 7.25 ppm (H phenyl+H$_3$ furan)—2 H at 6.70 ppm (H$_5$ thiazole+H$_4$ furan)—1 H at 5.65 ppm (H$_7$, D of D, J$_1$=8 Hz, J$_2$=5 Hz)—1 H at 5.09 ppm (H$_6$, D, J=5 Hz)—2 H at 4.15 ppm (C$\underline{\text{H}}_2$—S, AB, J$_{AB}$=14 Hz)—3 H at 3.78 ppm (C$\underline{\text{H}}_3$ ON, $\overline{\text{S}}$)—2 H at 3.47 ppm (C$\underline{\text{H}}_2$ in 2, AB, J$_{AB}$=16 $\overline{\text{Hz}}$).

(b) CM 31916

To 10 ml of an aqueous solution of 50% (volume/volume) formic acid heated to 57° C. are added 3 g of the tritylated product obtained previously. Stirring is effected for 20 minutes, maintaining the temperature at 57° C., then the mixture is cooled to ambient temperature. The triphenylcarbinol formed is filtered off and is washed with 5 ml of aqueous solution of 30% (volume/volume) formic acid.

To the filtrate are added 20 ml of absolute ethanol and evaporation is carried out to dryness in vacuo. The residue is taken up in 10 ml of absolute ethanol and the solid is dried without heat and washed with ether.

The solid is redissolved in a mixture of 100 ml of absolute ethanol and 50 ml of acetone then the solution is concentrated to 10 ml. The precipitate is dried without heat and is washed with absolute ethanol then with ether. After drying, 1 g of the expected product is obtained.

NMR spectrum (in solution in dimethylsulfoxide): 1 H at 9.50 ppm (N$\underline{\text{H}}$—CO, D, J=8 Hz)—1 H at 8.0 ppm (H$_5$ furan, S)—1 $\overline{\text{H}}$ at 7.37 ppm (H$_3$ furan, D, J=3 Hz)—2 H at 7.15 ppm (N$\underline{\text{H}}_2$, S.el)—2 H at 6.70 ppm (H$_4$ furan and H$_5$ thiazole)—1 H at 5.70 ppm (H$_7$, D of D, J$_2$=8 Hz J$_2$=5 Hz)—1 H at 5.10 ppm (H$_6$, D, J=5 Hz)—2 H at 4.05 ppm (C$\underline{\text{H}}_2$S, AB, J$_{AB}$=14 Hz)—3 H at 3.75 ppm (C$\underline{\text{H}}_3$ ON, S)—2 H at 3.50 ppm (C$\underline{\text{H}}_2$ in 2, AB, J$_{AB}$=16 Hz).

By replacing the 7-amino (furyl-2 carbonylthiomethyl)-3 cepheme-3 4-carboxylic acid by the corresponding acid in which the furyl radical has been replaced by a thienyl radical, the product CM 39917 is obtained, in which R$_3$ is

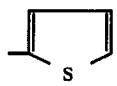

and A is H

NMR spectrum (in solution in dimethylsulfoxide): 1 H at 9.50 ppm (N$\underline{\text{H}}$—CO, D, J=8 Hz)—2 H at 7.92 ppm (H$_3$ thiophene and H$_5$ thiophene)—3 H at 7.20 ppm (N$\underline{\text{H}}_2$ and H$_4$ thiophene)—1 H at 6.70 ppm (H$_5$ thiazole, S)—1 H at 5.70 ppm (H$_7$, D of D, J$_1$=8 Hz, J$_2$=5 Hz)—1 H at 5.08 ppm (H$_6$, D, J=5 Hz)—2 H at 4.14 ppm (C$\underline{\text{H}}_2$—S, AB, J$_{AB}$=14 Hz)—3 H at 3.77 ppm (CH$_3$O$\underline{\text{N}}$,S)—2 H at 3.51 ppm (CH$_2$ in 2, AB, J$_{AB}$, J$_{AB}$=16 Hz).

EXAMPLE 2

Triethanolamine salt of syn isomer [(amino-2 thiazolyl-4)-2 methoxyimino-2 acetamido]-7 (thienyl-2 carbonylthiomethyl)-3 cepheme-3 4-carboxylic acid 0.5 g of the acid compound CM 31917 is dissolved in the mixture of 20 ml of absolute ethanol and 20 ml of acetone, then 0.13 g of triethanolamine is added and the mixture is concentrated in vacuo to 5 ml. 20 ml of ether are added and the precipitate is dried without heat and washed with ether. After drying in vacuo, 0.6 g of the expected salt is obtained.

NMR spectrum (in solution in dimethylsulfoxide): 1 H at 9.60 ppm (N$\underline{\text{H}}$CO, D J=8 Hz)—2 H at 8.0 ppm (H$_3$ and H$_5$ thiophene)—3 H at 7.25 ppm (NH$_2$ and H$_4$ thiophene)—1 H at 6.75 ppm (H$_5$ thiazole, S)—1 H at 5.70 ppm (H$_7$, D of D, J$_1$=8 Hz, J$_2$=5 Hz)—1 Hat 5.02 ppm (H$_6$, D, J=5 Hz)—2 H at 4.12 ppm (C$\underline{\text{H}}_2$S,M)—3 H at 3.82 ppm (CH$_3$O$\underline{\text{N}}$,S)—6 H at 3.67 ppm (C$\underline{\text{H}}_2$OH,-M)—2 H at 3.37 ppm (C$\underline{\text{H}}_2$ in 2, AB, J$_{AB}$=16 Hz)—6 H at 3.04 ppm

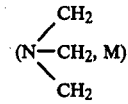

The products of the invention have been studied as far as their pharmacological properties, and more particularly bacteriostatic action, are concerned.

The in vitro bacteriostatic action was determined in a solid medium by the dilutions method. The study was directed to Gram+ and Gram− strains of which several are known for producing β lactamases.

The results are expressed in the minimum inhibitor concentrations (MIC—μg/ml).

The therapeutic efficacy of the products is determined in the septicaemic model of the mouse.

Septicaemia is provoked by intraperitoneal inoculation of 0.5 ml of an appropriate dilution of suspension of the strain E.coli Sol. RL 90 producing cephalosporinase.

The products are administered in solution in a phosphate buffer pH 7.0 in a volume of 0.2 ml by the subcutaneous route and at a rate of 5 doses (mg of product per kg of live weight of mouse) to batches of 10 mice 1 hour and 5 hours after inoculation of the germ.

After 4 days of observation during which the mortality is noted, the median effective doses (ED 50) are calculated by the Muench and Reed method.

The results obtained are shown in Table I hereinafter. These results clearly show the considerable activity of the products both on the bacteria not producing β lactamases and on the producing strains.

Furthermore, the tests made up to the present time on animals have not shown any particular toxicity for the products according to the invention.

The products of the invention may therefore be used as antibiotics in human or veterinary medicine. They have a broad spectrum of activity and may be used in all bacterial infections with sensitive germs.

The products may be administered by the oral, rectal, injectable or local route.

The pharmaceutical compositions are made from compounds (I) in their acid form or, when their solubility is insufficient, in the form of a salt. Thus, the sodium salt of compound CM 31916 has a solubility greater than 20% in a buffer solution having a pH of 7.

The pharmaceutical compositions may be solid or liquid and may be, for example, in the form of tablets, gelatin-coated pills, granules, suppositories, ointments, creams, gels or injectable preparations.

Dosage may vary to a large extent, in particular depending on the type and seriousness of the infection to be treated and depending on the mode of administration. In the adult, by injectable route, it is most often between 0.250 g and 4 g per day.

By way of example of pharmaceutical composition, ampoules containing:

CM 31916 Sodium salt: 1.10 g
Water for injectable preparation: 4 ml
may be prepared.

and easily hydrolyzable or metabolically labile ester radicals, and $R_3$ is a radical selected from the group consisting of 2-furyl radicals and 2-thienyl radicals.

2. A compound according to claim 1 in the syn isomer form.

3. A compound according to claim 1 wherein the group

is a triethyl amine salt.

TABLE I

| | Strains | | | | | | |
|---|---|---|---|---|---|---|---|
| | not producing lactamases | | | producing lactamases | | | |
| | | | | | | Klebsiella pneumoniae RO 30 | Septicaemia provoked in the mouse by Escherichia coli SOL RL 90 DE 50 (mg/kg) |
| No. of Products | Staphylococcus aureus Smith | Escherichia coli A 223 IP | Klebsiella pneumoniae E 55 | Escherichia coli R 69/2 TEM | Escherichia coli SOL RL 90 | | |
| 31 916 | 0.25 | 0.5 | 1 | 0.25 | 2 | 8 | 5.4 |
| 31 917 | 0.25 | 0.5 | 1 | 0.5 | 2 | 8 | 3.6 |

What is claimed is:

1. A compound corresponding to the formula

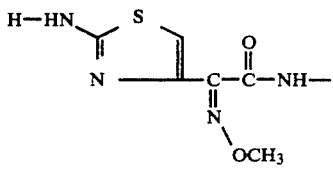

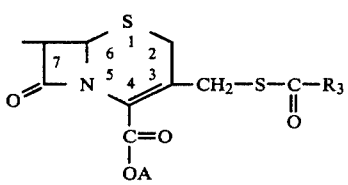

wherein:
the group

in the 4 position is a pharmaceutically acceptable radical selected from the group consisting of acid radicals, alkali salts, alkaline earth salts, amine salts 4. A compound according to claim 1 wherein the group $$-\overset{O}{\underset{\|}{C}}-OA$$

is an ethanolamine salt.

5. A compound according to claim 1 wherein $R_3$ is a 2-furyl group.

6. A compound according to claim 1 wherein $R_3$ is a 2-thienyl group.

7. A compound according to claim 2 wherein A represents hydrogen and $R_3$ represents 2-furyl.

8. A compound according to claim 2 wherein A represents hydrogen and $R_3$ represents 2-thienyl.

9. A compound according to claim 2 wherein A represents sodium and $R_3$ represents 2-furyl.

10. A compound according to claim 2 wherein A represents triethanolammonium and $R_3$ represents 2-thienyl.

11. A drug comprising as active substance an effective antibiotic amount of at least one compound according to claim 1.

12. An injectable drug composition according to claim 11 comprising water and from 0.25 to 4 g. of said compound.

* * * * *